United States Patent

Grabenkort et al.

[11] Patent Number: 5,238,010
[45] Date of Patent: Aug. 24, 1993

[54] CATHETER SITE SHIELD

[75] Inventors: Richard W. Grabenkort, Barrington, Ill.; Mary M. Carey, Kirkland; Conrad T. O. Fong, Redmond, both of Wash.

[73] Assignee: Abbott Laboratories, Mountain View, Calif.

[21] Appl. No.: 777,819

[22] Filed: Oct. 11, 1991

[51] Int. Cl.⁵ ............................................. A61F 13/00
[52] U.S. Cl. ................................... 128/888; 128/846
[58] Field of Search .............. 128/845, 846, 877, 878, 128/879, 887, 888

[56] References Cited

U.S. PATENT DOCUMENTS

| | | | |
|---|---|---|---|
| 695,270 | 3/1902 | Beringer | 128/888 |
| 2,831,487 | 4/1958 | Tafilaw | 128/350 |
| 3,059,645 | 10/1962 | Hasbrouck | 128/346 |
| 3,194,235 | 7/1965 | Cooke | 128/888 |
| 3,304,938 | 2/1967 | Perkins, Jr. | 128/888 |
| 3,782,377 | 1/1974 | Rychlik | 128/132 |
| 3,900,026 | 8/1975 | Wagner | 128/888 |
| 3,901,226 | 8/1975 | Scardenzan | 128/888 |
| 4,134,399 | 1/1979 | Halderson | 128/888 |
| 4,397,647 | 8/1983 | Gordon | 604/180 |
| 4,449,975 | 5/1984 | Perry | 604/179 |
| 4,470,410 | 9/1984 | Elliott | 128/133 |
| 4,517,971 | 5/1985 | Sorbonne | 128/133 |
| 4,561,857 | 12/1985 | Sacks | 604/174 |
| 4,591,356 | 5/1986 | Christie | 604/179 |
| 4,633,863 | 1/1987 | Filips et al. | 128/846 |
| 4,641,641 | 2/1987 | Strock | 128/888 X |
| 4,679,553 | 7/1987 | Proulx et al. | 128/846 |
| 4,846,807 | 7/1989 | Safadago | 604/179 |
| 4,870,976 | 10/1989 | Denny | 128/877 |
| 4,898,587 | 2/1990 | Mera | 604/174 |
| 4,919,150 | 4/1990 | Grant | 128/877 |
| 4,982,744 | 1/1991 | Stanec | 128/877 |
| 4,982,745 | 1/1991 | Shields | 128/877 |

Primary Examiner—Robert A. Hafer
Assistant Examiner—Sam Rimell
Attorney, Agent, or Firm—Harry G. Thibault; Robert E. Wexler

[57] ABSTRACT

An improved site protector of simple one-piece construction includes a convex tapered bubble as the main body portion, and a plurality of aeration openings defined at step-down portions of the bubble, the step-down portions providing strength, stability and rigidity to the bubble. A locking member provided at one end of the site protector stabilizes the catheter at the insertion site.

6 Claims, 4 Drawing Sheets

CATHETER SITE SHIELD

BACKGROUND OF THE INVENTION

1. Field of the Invention

The present invention relates generally to the field of intravenous catheters and more particularly to an improved site shield for protecting and stabilizing a catheter inserted into the body of a patient

2. Description of the Prior Art

When an intravenous catheter is installed into the arm of the patient, it is necessary to stabilize the position of the catheter to assure that it remains properly installed in the patient for the duration of the procedure to be conducted intravenously, whether it be a blood transfusion requiring moments of stabilization, an intravenous feeding which could require an hour or more, or continuous intravenous readings associated with a sensor inserted into the blood stream of a patient, those readings taken over a period of hours or even days.

A variety of shields are known for site protection. For example, U.S. Pat. No. 4,679,553, entitled "Venipuncture Site Protector" Prouix et al, discloses a relatively rigid cup-like shield of frustro-pyramidal shape having mountings tabs extending from the shield, which tabs are taped to the patient's body with the shield positioned over the venipuncture site. However, such a device is typically not appropriate for a site in which an elongated catheter has been inserted in the body, fails to provide a locking feature for such catheter and may not provide sufficient ventilation to the site.

A more elongated device can be seen in U.S. Pat. No. 3,901,226, entitled "Protective Guard for a Hypodermic Needle"—Scardenzan, but such device also fails to provide a locking feature for the catheter. Moreover, the inherent flexibility designed in each of the above two devices would tend to provide less rigidity at the catheter site and thus make the catheter susceptible to jarring or bumping which could flex the protector and cause the catheter to be moved out of position or even jarred from the body of the patient.

Attempts to further stabilize the catheter site can be seen in U.S. Pat. No. 4,517,971, entitled "Guard for Venipuncture Site and Catheter Retainer"—Sorbonne, and U.S. Pat. No. 4,898,587, entitled "Intravenous Line Stabilizing Device"—Mera. Such devices attempt to stabilize the catheter by introducing complexities into the structure of the site protector device such as by providing a base for the site protector, as well as an upper cover. Such devices address the problem of site stabilization by introducing complexities and additional parts to the site protector.

Typically what is needed with respect to a site protector is a locking feature over the catheter to protect the needle/tubing junction of the catheter from accidental disconnection. Disconnection of the needle/tubing junction, typically a luer lock fitting provided between the needle and the tubing at such junction, could be very serious, particularly if an arterial line is involved. Such a locking feature also prevents kinking of the needle/tubing junction which is a major contributor to loss of arterial lines because a severely kinked catheter will compromise continuous blood pressure monitoring.

The site protector should be long enough to protect both the insertion site and the distal end of the catheter which can be three or more inches long. A preferred site protector should be relatively flexible to be compatible with the placement of venous or arterial catheters in all common access locations on both adult and pediatric patients. Even though the preferred site protector must be flexible, it must also be rigid overlying the site location to protect the insertion site and the catheter therein from inadvertent bumps and jars commonly experienced in the medical procedures associated therewith.

It is desirable that a site protector of the preferred configuration properly ventilate the site and yet be smooth and conforming to the patient It is further desirable that the improved site protector be made of a clear material to make it possible for the care giver to view the catheterization site without need to remove the site protector. While it is known to strap a site protector to the patient, too tight a strap can interfere with circulation, and it is desirable to be able to tape down the site protector and have it adaptable to all size limbs rather than to strap the site protector or catheterization site, to minimize interference with circulation. It would further be advantageous if the site protector were of a simplified configuration permitting ease of manufacture and further being relatively inexpensive to manufacture.

SUMMARY OF THE INVENTION

In accordance with the present invention, an improved site protector or site shield has been devised. The site protector of the present invention comprises a one-piece clear plastic device having an elongate tapered convex main body portion with an outer flange disposed at the distal end and a locking hub provided a the proximal end thereof, with lateral straps protruding from opposite sides of the main body portion.

The central bubble of the main body portion of the improved site protector is relatively convex and includes therein a number of aeration sites to permit sufficient ventilation to the venipuncture site. The aerating holes in the central bubble are accompanied by suitable channels concentric therewith which strengthen and stabilize the central bubble while providing a substantial plurality of aeration openings therein.

The locking member provided at the distal end of the catheter captures the luer lock hub at the catheter/tubing junction, thus to properly position the site protector relative to the catheter at the insertion site as well as to protect that junction from accidental disconnection.

The central body portion of the site protector is generously flanged with a forward flange extending forward of the distal end of the bubble and a rear flange extending rearward of the locking member enabling the site protector to be stabilized on the limb of the patient at the insertion site. The flexible side members provide additional stabilization of the site protector at the insertion site.

The on piece construction of the improved site protector makes it very inexpensive and extremely easy to manufacture.

Other features and advantages of the improved site protector of the present invention will be ascertained upon a reading of the detailed description thereof, particularly when such detailed description is considered in conjunction with the attached drawings.

DETAILED DESCRIPTION OF THE PREFERRED EMBODIMENT

Figure 1:
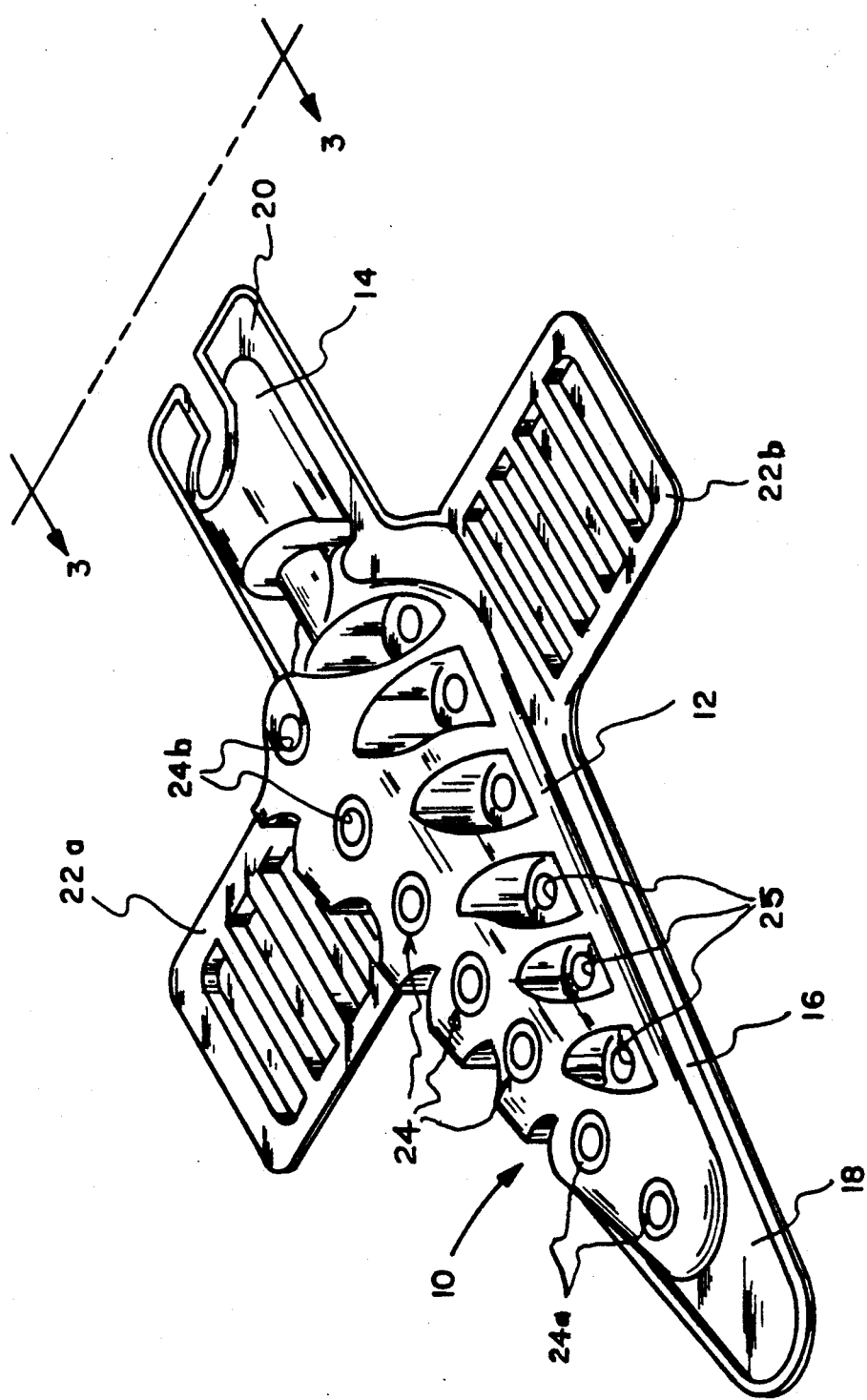
FIG. 1 is a top right perspective view of the improved site protector of the present invention.
Figure 2:
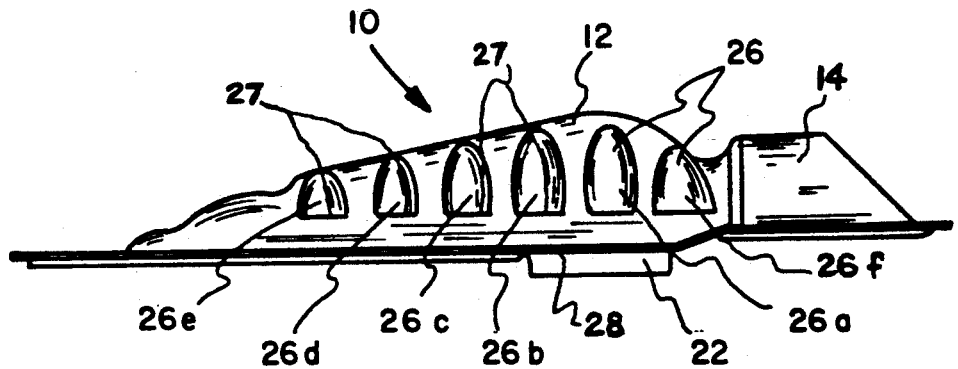
FIG. 2 is a side elevation of the site protector of FIG. 1.
Figure 3:
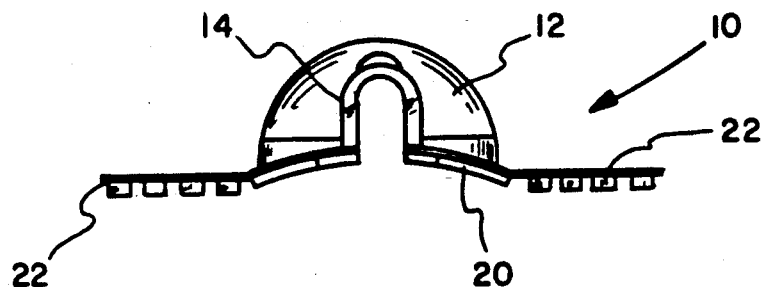
FIG. 3 is an end view of the site protector, taken generally along the lines 3—3 of FIG. 1.

FIGS. 1-3 disclose an improved site protector or site shield 10 usable when a catheter 11 or similar device is installed in the arm of a patient. The site protector 10, best seen in FIG. 1, comprises a convex bubble-like central body portion 12 having a locking member 14 extending from the distal end thereof and including a generous peripheral flange 16 which surrounds the central body portion 12, as well as the locking member 14, and includes a forward flange portion 18, extending forwardly of the front end of the bubble 12 and a rear flange 20 extending rearward of the locking member 14. Also provided on the flange 16 are lateral extensions or wings 22a and 22b which extend laterally from the side of the site protector 10. Wings 22a and 22b are ribbed for increased flexibility.

As better seen in FIG. 2, the bubble 12 is tapered from its proximal end to its distal end to better overlie and accommodate an elongated catheter 30 (FIG. 5) and an associated luer lock hub provided between tubing 29 and the catheter 30.

A plurality of aeration sites 24 are provided in the bubble 12. The aeration sites 24 include step-down portions 24a to provide structural rigidity and stability to the bubble 12. Aeration sites 24 extend generally along a longitudinal axis of the site protector 10 and include a series of generally equally spaced openings 24b concentric with step-down portions 24a.

A series of step-down channels 26 are also provided on opposite sides of the bubble 12 and generally disposed to lie between the openings 24 and the peripheral flange 16. The base 27 of each channel 26 is generally equally spaced from a base 28 of the site protector 10, with the respective upper end of each step-down channel 26 extending generally to the upper end of the bubble 12, thus to proceed along the face of the bubble 12, with the tallest channel 26a near a distal end of the bubble 12 and the channels decreasing generally in size from channel 26a through channels 26b,c,d and e of the bubble 12. The apex of a channel 26f between channel 26a and the locking member 14 lies below the apex of channel 26a and is closest in height to step-down channel 26c. Aeration openings 25 are provided in the base 27 of each channel 26 and concentric therewith. The opposite side of the bubble 12 is similarly configured.

Such step-down channels 26 give the bubble 12 substantially greater strength than conventional designs; yet such strength is accomplished in an easily molded device of simple one piece construction.

The locking portion 14 of the site protector 10 includes a generally semi-circular opening 28 for receiving the fluid delivery line 29 associated with the catheter 30 and retains the catheter/tubing joint within the site protector at the catheterization site.

The improved site protector 10 of the present invention comprises a simply manufactured one-piece structure which incorporates a relatively rigid central bubble of clear plastic material and having a tapered length sufficient to protect a catheterization site in which an elongated catheter 30 is inserted into the patient. Aeration openings 24,25 are provided in the central bubble portion 12 of the site protector to assure adequate aeration of the catheter site. Moreover, aeration is provided by installing certain of the aeration openings 25 in bases 27 of respective channels 26 of the central bubble, to be concentric therewith, the channels 26 to increase rigidity of the central bubble and further protect the catheterization site.

Figure 5:
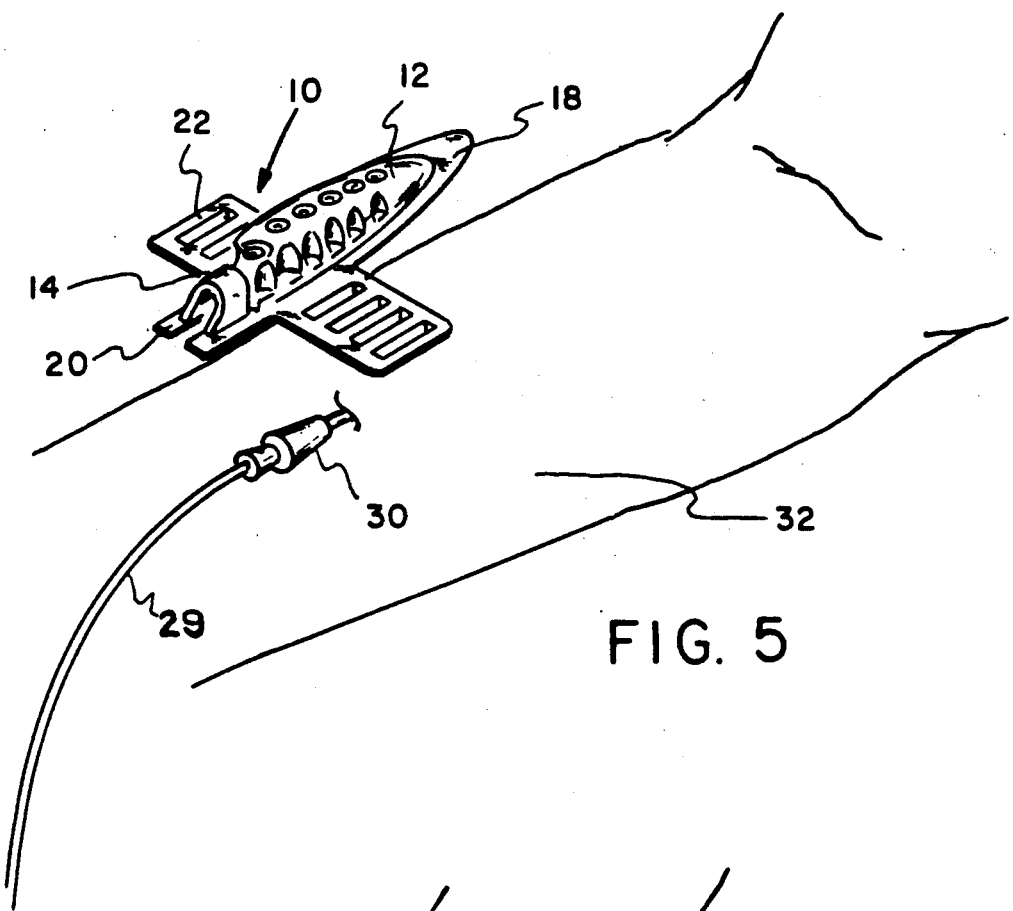
FIG. 5 is an exploded perspective view of FIG. 4, with the site protector displaced from the forearm of the patient to show the proper orientation of the catheter with respect to the site protector.
Figure 4:
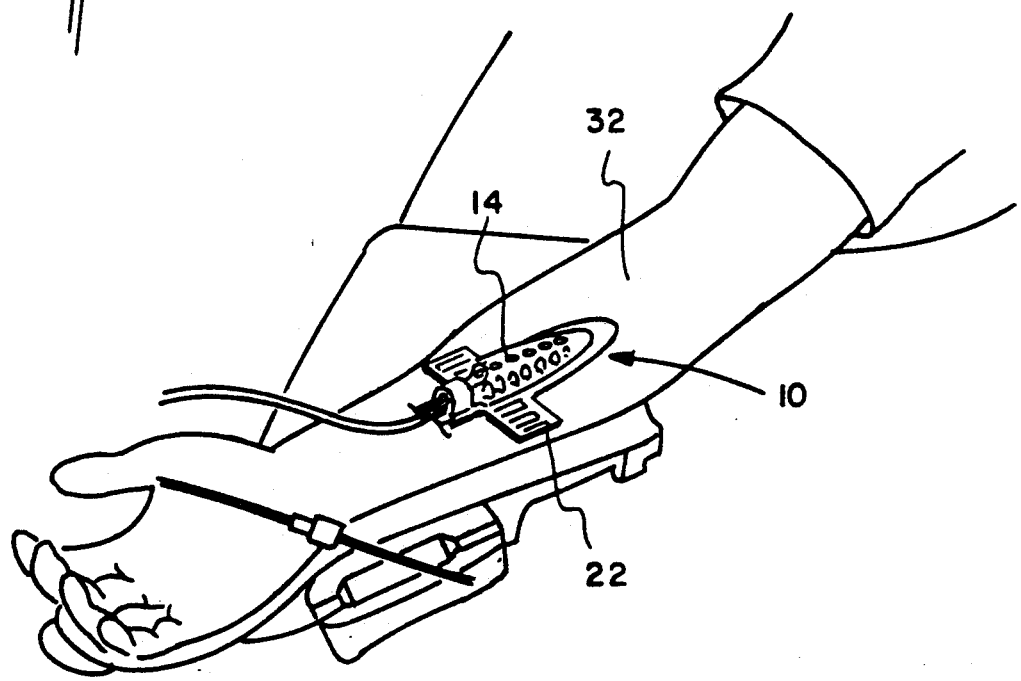
FIG. 4 is a top perspective view of the site protector of the present invention installed in place on the forearm of a patient.
Figure 6:
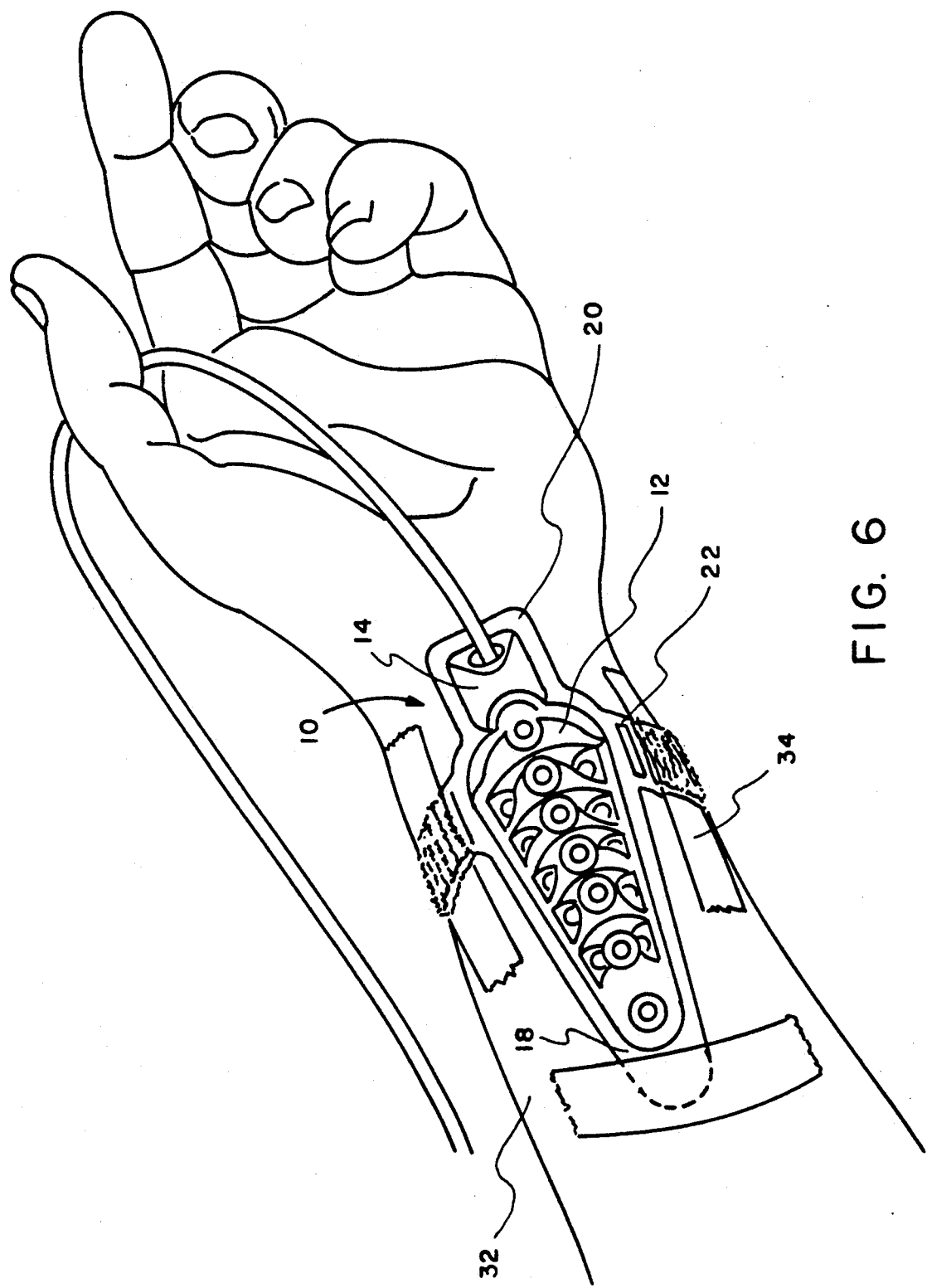
FIG. 6 is an enlarged perspective view, showing catheter in place and the site protector of the present invention fully installed and overlying the catheter inserted in the forearm of the patient.

As shown in FIGS. 4-6, the locking member 14 assures that the catheter 30 inserted into the forearm 32 of a patient is stabilized and held in that stabilized position for the duration of the procedure to be conducted on the patient. Moreover, the generous front flange portion 18 and proximal flange portion 20 assures that the site protector 10 can be readily fixed to the patient.

Moreover, the ribbed lateral straps 22 conform to the shape of the patient's arm to give additional flexibility to positioning the site protector 10 on the limbs of the patient, thus assuring that the site protector 10 is adaptable to any number of positional locations on the patient. The site protector is then secured to the patient's forearm 32 at wings 22, front flange 18 and rear flange 20 by tape strips 34.

In the preferred embodiment, the bubble 12 is made of clear plastic, to readily enable the caregiver to view the catheterization site without removing the site protector 10. Moreover, the bubble 12 is tapered, to accommodate a catheter 30 of substantial length, and generally conforms to the patient's body at the catheterization site and provides a relatively low profile at the site, making it less likely that the site protector 10 can snag on bed clothes, sheets, etc. and be accidentally removed.

Having defined a preferred embodiment of the present invention, it is clear that variations can be made therein without departing from the intent and scope of the present invention. The claims set forth below define the scope of the present invention.

We claim:

1. An improved site protector for a catheter insertion site of a patient, said site protector comprising a one-piece device having:

a main body portion including an elongated central convex bubble extending upwardly from the main body portion;

plurality of aeration sites distributed on an upper surface of the bubble, each aeration site comprising a stepped-down portion stepped in from said upper surface of the bubble and each stepped-down portion including respective sidewalls and a base portion and receiving an aeration opening in said base portion, each respective aeration opening generally concentric with the base of its respective stepped down portion the aeration sites provided in the bubble to substantially improve the strength and stability of the bubble;

a locking member provided at the proximal end of the site protector and connected to the central convex bubble thereof; and a peripheral flange extending around the main body portion of the site protector, rearwardly of the locking member, and forwardly of the forward end of the bubble, with lateral extensions of the peripheral flange provided on the opposite sides of the bubble to generally conform the site protector to the site chosen for installation of the catheter in the patient.

2. An improved site protector as claimed in claim 1 wherein the offsets at the aeration sites include a first plurality of step-down portions disposed along a longitudinal axis of the bubble of the site protector, such step-down portions concentric with aeration openings disposed along the longitudinal axis of the site protector.

3. An improved site protector as claimed in claim 2 wherein a second plurality of step-down portions include a series of step-down channels disposed between the longitudinal axis of the bubble and the peripheral flange thereof on opposite sides of the bubble, with an aeration opening provided in a base of each step-down channel defined on the bubble, each aeration opening generally concentric with a respective base of a step-down channel.

4. An improved site protector as claimed in claim 1 wherein the one-piece site protector is formed from a clear plastic to enable viewing of the catheter insertion site without removing the site protector.

5. An improved site protector as claimed in claim 1 wherein the bubble is tapered from front to rear to better conform to the catheter insertion site and to present a low profile when installed on a patient.

6. An improved site protector as claimed in claim 1 wherein the locking member retains a catheter/tubing joint to stabilize the catheter at the insertion site.

* * * * *